United States Patent
Refvik et al.

(12) 
(10) Patent No.: US 6,506,721 B1
(45) Date of Patent: Jan. 14, 2003

(54) DETERGENT ADDITIVE COMPOSITION AND PROCESSES THEREFORE AND THEREWITH

(75) Inventors: Mitchell D. Refvik; David W. Dockter, both of Bartlesville, OK (US)

(73) Assignee: Phillips Petroleum Company, Bartlesville, OK (US)

( * ) Notice: Subject to any disclaimer, the term of this patent is extended or adjusted under 35 U.S.C. 154(b) by 0 days.

(21) Appl. No.: 09/667,654

(22) Filed: Sep. 22, 2000

Related U.S. Application Data

(60) Provisional application No. 60/159,846, filed on Oct. 15, 1999.

(51) Int. Cl.$^7$ .......................... C11D 3/34; C07C 215/08
(52) U.S. Cl. ........................................ 510/492; 564/396
(58) Field of Search ................................ 510/499, 492; 564/396, 471

(56) References Cited

U.S. PATENT DOCUMENTS 2,281,521 A * 4/1942 Fuller .......................... 252/47
4,402,842 A * 9/1983 Horodysky et al. ........ 252/47.5

FOREIGN PATENT DOCUMENTS

EP 93601 A1 * 11/1983
EP 473542 A1 * 3/1992

OTHER PUBLICATIONS

H. Boehme et al., Chemische Berichte, 1970, vol. 103, 3058, abstract, no month available.*

* cited by examiner

*Primary Examiner*—John Hardee
(74) *Attorney, Agent, or Firm*—Charles W. Stewart

(57) ABSTRACT

A novel composition having the formula:

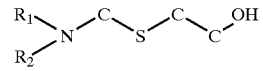

wherein $R_1$ is selected from the group consisting of an alkyl group containing from 1 to 20 carbon atoms and an aryl group, and $R_2$ is selected from the group consisting of an alkyl group containing from 1 to 20 carbon atoms and an aryl group. The composition is made by combining an amine compound, a carbonyl compound, a solvent, and a sulfur-containing compound. The composition is used as a detergent additive in cleaning process.

16 Claims, No Drawings

DETERGENT ADDITIVE COMPOSITION AND PROCESSES THEREFORE AND THEREWITH

This application claims the benefit of U.S. Provisional Application Serial No. 60/159,846, filed Oct. 15, 1999.

This invention relates to a novel composition useful as a detergent additive and processes for making and using such composition.

BACKGROUND OF THE INVENTION

Commercial and household detergent compounds are well known. Improved detergents are constantly being developed to provide less expensive, more environmentally friendly, and more effective cleaning products.

The effectiveness of a detergent can be measured in many different ways. The most obvious measure of a detergent's effectiveness is its ability to remove undesirable compounds from a base material without negatively impacting the properties of the base material; however, depending on the function for which a specific detergent is intended, its effectiveness is measured in other ways. The effectiveness of laundry detergent, for example, can be measured by its ability to dissolve in water, minimize suds, prevent calcium build-up, soften fabrics, and clean multiple fabrics.

New detergent additives are frequently mixed with existing detergents or substituted for less desirable detergent components in order to decrease cost, increase effectiveness, and produce more environmentally friendly detergents.

It is therefore an object of the present invention to provide a novel composition which, when admixed with a detergent, will create an economically feasible, environmentally friendly, and/or more effective detergent.

It is further an object of the present invention to provide methods for making and using such novel composition.

Other objects and advantages of the present invention will become apparent from the description, the example, and the appended claims.

SUMMARY OF THE INVENTION

In a first embodiment of the present invention a novel composition is provided. The novel composition has the following formula:

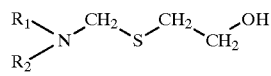

wherein $R_1$ is selected from the group consisting of an alkyl group containing from 1 to 20 carbon atoms and an aryl group; and $R_2$ is selected from the group consisting of an alkyl group containing from 1 to 20 carbon atoms and an aryl group.

In a second embodiment of the present invention a process of making the above-described novel composition is provided. The process comprises the following steps: (a) combining an amine compound, a carbonyl compound, and a solvent compound to produce a first product; (b) combining the first product and a sulfur-containing compound to produce a second product; and, (c) separating the second product to obtain a substantially pure quantity of the novel composition described in the first embodiment of the present invention.

In a third embodiment of the present invention a process of using the above-described novel composition is provided. The process comprises the following steps: (a) admixing the novel composition described in the first embodiment of the present invention with a detergent composition to produce a modified detergent composition; and, (b) contacting the modified detergent composition with an undesirable compound attached to a base material.

DETAILED DESCRIPTION OF THE INVENTION

According to a first embodiment of the present invention, a novel composition useful as a detergent additive has been discovered. The novel composition comprises, consists of, or consists essentially of, a composition having the following formula:

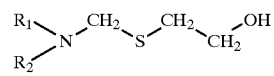

wherein $R_1$ is selected from the group consisting of an alkyl group containing from 1 to 20 carbon atoms and an aryl group; and $R_2$ is selected from the group consisting of an alkyl group containing from 1 to 20 carbon atoms and an aryl group. Preferred aryl groups include a phenyl group and a substituted phenyl group including a phenyl substituted with both a hydroxy and a methyl. Preferred alkyl groups include alkyl groups containing from 1 to 6 carbon atoms. More preferred alkyl groups include the substituents of ethyl, methyl, propyl, butyl, 2-hydroxy ethyl, and 3-hydroxy propyl. Even more preferably each of $R_1$ and $R_2$ is an ethyl group. Most preferably the novel composition is diethylaminomethyl 2-hydroxyethylsulfide.

According to a second embodiment of the present invention, a process for making the novel composition described in the first embodiment of the present invention has been discovered. Such process of making comprises the following steps: (a) combining under reaction conditions an amine compound, a carbonyl compound, and a solvent compound to produce a first product; (b) combining under reaction conditions the first product and a sulfur-containing compound to produce a second product; and, (c) separating the second product to obtain a substantially pure quantity of the novel composition described in the first embodiment of the present invention.

The amine compound employed in step (a) can be any amine compound capable of reacting with a carbonyl compound. Preferably the amine compound is a secondary amine compound. More preferably the amine compound is a compound selected from the group consisting of diethylamine, dimethylamine, diethanolamine, N-ethylmethylamine, dipropylamine, diisopropylamine, dibutylamine, diphenylamine, dibenzylamine, dialkylamine, and diisobutylamine. Most preferably the amine compound is diethylamine.

The carbonyl compound employed in step (a) can be any carbonyl compound capable of reacting with an amine. Preferably the carbonyl compound is aldehyde or a ketone. More preferably the carbonyl compound is an aldehyde compound selected from the group consisting of formaldehyde and paraformaldehyde. Most preferably the carbonyl compound is paraformaldehyde.

The solvent compound employed in step (a) can be any solvent compound capable of dissolving the amine compound and the carbonyl compound. Preferably the solvent compound is an aromatic hydrocarbon capable of forming an azeotrope with water. More preferably the solvent compound is a compound selected from the group consisting of toluene, benzene, and xylenes. Most preferably the solvent compound is toluene.

The first product, produced in step (a), can be any composition or mixture of compositions produced by combining the amine compound, the carbonyl compound, and the solvent compound and capable of reacting with a sulfur-containing compound. The first product can comprise unreacted reactants, water, products from the reaction of the amine compound and the carbonyl compound, and products from side reactions.

The individual quantities of the amine compound, the carbonyl compound, and the solvent compound combined in step (a) can be any quantities effective to produce the first product. Preferably the quantities of the compounds employed in step (a) provide a molar ratio of the amine compound to the carbonyl compound of from about 10:1 to about 1:10, preferably from about 5:1 to about 1:2, and most preferably from 1.3:1 to 1:1.3. Preferably the molar ratio of the solvent compound to the carbonyl compound is less than about 100:1, more preferably less than about 10:1, even more preferably less than about 5:1, and most preferably less than 1:1.

The amine compound, the carbonyl compound, and the solvent compound may be combined in step (a) under reaction conditions sufficient to produce the first product. Preferably the reaction conditions include a temperature in the range of from about 0° C. to about 300° C., more preferably from about 5° C. to about 250° C., and most preferably from 10° C. to 200° C.; and a pressure in the range of from or about below atmospheric to or about 5 atmospheres, more preferably from about atmospheric to about 3 atmospheres, and most preferably from atmospheric to 2 atmospheres.

Between steps (a) and (b) it may be desirable to remove water from the first product. Water may be removed from the first product using any suitable method know in the art. Preferred methods of removing water from the first product include azeotropic distillation, absorption, and chemical reaction. Azeotropic distillation is presently the most preferred method of water removal.

The sulfur-containing compound employed in step (b) can be any mercaptan capable of reacting with the first product. Preferably the sulfur-containing compound is an alkyl mercaptan or heteroatom-substituted mercaptan. More preferably the sulfur-containing compound is a compound selected from the group consisting of methyl mercaptan, ethyl mercaptan, 2-hydroxyethanethiol, and 3-hydroxypropanethiol. Most preferably the sulfur-containing compound is 2-hydroxyethanethiol.

The second product, produced in step (b), can be any composition or mixture of compositions produced by combining the first product with the sulfur-containing compound and containing a quantity of the novel composition described in the first embodiment of the present invention. The second product can comprise unreacted reactants, water, and products from side reactions, in addition to the novel composition described in the first embodiment of the present invention. Preferably the second product contains the novel composition described in the first embodiment of the present invention in an amount greater than about 5%, preferably greater than about 25%, even more preferably greater than about 50%, and most preferably greater than about 75% by weight.

The quantity of the sulfur-containing compound combined with the first product in step (b) can be any quantity effective to make the second product. Preferably the quantity of the sulfur-containing compound employed in step (b) should be a quantity which would provide a molar ratio of the sulfur-containing compound to the amount of carbonyl compound employed in step (a) of from about 10:1 to about 1:10, preferably from about 5:1 to about 1:2, and most preferably from 1.3:1 to 1:1.3.

The first product and the sulfur-containing compound may be combined in step (b) under reaction conditions sufficient to produce the second product. Preferably the reaction conditions include a temperature in the range of from about 0° C. to about 300° C., more preferably from about 5° C. to about 250° C., and most preferably from 10° C. to 200° C.; and a pressure in the range of from or about below atmospheric to or about 5 atmospheres, more preferably from about atmospheric to about 3 atmospheres, and most preferably from atmospheric to 2 atmospheres.

Between steps (b) and (c) it may be desirable to remove water from the second product. Water may be removed from the second product using any suitable method know in the art. Preferred methods of removing water from the second product include azeotropic distillation, absorption, and chemical reaction. Azeotropic distillation and absorption are presently the most preferred methods of water removal.

In step (c) the second product is separated to obtain a substantially pure quantity of the novel composition described in the first embodiment of the present invention. The "substantially pure quantity" preferably contains the novel composition described in the first embodiment of the present invention in an amount greater than about 25%, preferably greater than about 50%, even more preferably greater than about 75%, and most preferably greater than about 95% by weight. Separation of the second product can be accomplished by any suitable separation method know in the art, with the presently most preferred method being fractional distillation.

According to a third embodiment or the present invention, a process of using the novel composition described in the first embodiment of the present invention comprises, consists of, or consists essentially of the following steps: (a) admixing the novel composition described in the first embodiment of the present invention with a detergent composition to produce a modified detergent composition; and, (b) contacting the modified detergent composition with an undesirable compound attached to a base material. The conditions under which the contacting step occur are cleaning conditions sufficient to remove at least a portion of the undesirable compound from the base material.

The novel composition described in the first embodiment of the present invention can be added to and mixed with any known detergent composition in any manner known in the art, including for example, blending, stirring, and shaking. The quantity of the novel composition described in the first embodiment of the present invention added to the detergent composition can be an amount which decreases the cost, decreases the toxicity, or increases the effectiveness of the detergent composition.

The contacting of the modified detergent composition and the undesirable compound attached to the base material preferably takes place under cleaning conditions which enhance the effectiveness of the modified detergent composition. Such detergent effectiveness-enhancing conditions include, for example, elevated temperatures, elevated pressures, and elevated moisture. For laundry detergents, the contacting conditions can be any standard laundering conditions produced in a commercial or household automatic washing machine.

The following example is presented to further illustrate the present invention and is not to be considered as limiting the scope of the invention.

EXAMPLE

The following example demonstrates a method of preparing the novel composition of the present invention.

A 2 liter, 3-neck round bottom flask was equipped with a magnetic stirrer, thermowell, 250 ml pressure equalizing addition funnel with reflux separator, and Dean Stark trap with reflux condenser. To this system 90.1 g of paraformaldehyde (3.0 mole), 100 ml of toluene, and 341 ml diethylamine (3.3 mol, 241.4 g) were charged. The system was then refluxed and water produced was removed from the Dean Stark trap. When water was no longer produced at the Dean Stark trap the 231.5 ml of 2-hydroxyethanethiol (3.3 mol, 257.9 g) was slowly added to the refluxing system. The system was then refluxed and the water produced was removed from the Dean Stark trap. When water was not longer produced the kettle was cooled. The reaction solution was dried over anhydrous $Na_2SO_4$. The lights were then stripped under vacuum and the product distilled at 1 torr. Product fraction distilled between 143° C. and 145° C. at 1 torr.

What is claimed is:

1. A composition comprising a detergent composition and the following formula:

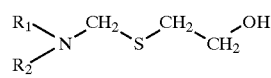

wherein $R_1$ is selected from the group consisting of an alkyl group containing from 1 to 20 carbon atoms and an aryl group; and $R_2$ is selected from the group consisting of an alkyl group containing from 1 to 20 carbon atoms and an aryl group.

2. A composition according to claim 1 wherein $R_1$ and $R_2$ are each selected from the group consisting of a phenyl group, a substituted phenyl group, an ethyl group, a methyl group, a propyl group, a butyl group, a 2-hydroxy ethyl group, and a 3-hydroxy propyl group.

3. A composition according to claim 1, wherein $R_1$ and $R_2$ are both an ethyl group.

4. A process of making a composition comprising the following formula:

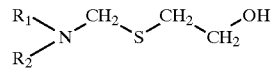

wherein $R_1$ is selected from the group consisting of an alkyl group containing from 1 to 20 carbon atoms and an aryl group; and $R_2$ is selected from the group consisting of an alkyl group containing from 1 to 20 carbon atoms and an aryl group, said process comprises the steps: (a) combining an amine compound, a carbonyl compound, and a solvent compound to produce a first product; (b) combining said first product and a sulfur-containing compound to produce a second product; and (c) separating said second product to obtain a substantially pure quantity of said composition.

5. A process according to claim 4 wherein said amine compound is a secondary amine compound.

6. A process according to claim 5 wherein said carbonyl compound is selected from the group consisting of an aldehyde and a ketone.

7. A process according to claim 6 wherein said solvent compound is an aromatic hydrocarbon.

8. A process according to claim 4 wherein said sulfur-containing compound is selected from the group consisting of an alkyl mercaptan and a heteroatom-substituted mercaptan.

9. A process according to claim 8 wherein the molar ratio of said amine compound to said carbonyl compound employed in step (a) is from about 5:1 to about 1:2.

10. A process according to claim 9 wherein the molar ratio of said solvent compound to said carbonyl compound employed in step (a) is less than about 10:1.

11. A process according to claim 10 wherein said amine compound is diethylamine.

12. A process according to claim 11 wherein said carbonyl compound is paraformaldehyde.

13. A process according to claim 12 wherein said solvent is toluene.

14. A process according to claim 13 wherein said sulfur-containing compound is 2-hydroxyethanethiol.

15. The composition according to claim 14 wherein $R_1$ and $R_2$ are both an ethyl group.

16. A process of using a composition comprising the following formula:

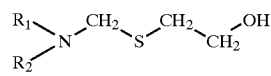

wherein $R_1$ is selected from the group consisting of an alkyl group containing from 1 to 20 carbon atoms and an aryl group; and $R_2$ is selected from the group consisting of an alkyl group containing from 1 to 20 carbon atoms and an aryl group, said process comprises the steps: (a) admixing said composition with a detergent composition to produce a modified detergent composition; and (b) contacting under cleaning conditions said modified detergent composition with an undesirable compound attached to a base material, wherein said cleaning conditions are sufficient to remove at least a portion of said undesirable compound from said base material.

* * * * *